(12) United States Patent
Song et al.

(10) Patent No.: US 7,667,462 B2
(45) Date of Patent: Feb. 23, 2010

(54) NUCLEAR MAGNETIC RESONANCE MODULE

(75) Inventors: Yi-Qiao Song, Ridgefield, CT (US); Richard Gaylor, Brookfield, CT (US)

(73) Assignee: Schlumberger Technology Corporation, Cambridge, MA (US)

( * ) Notice: Subject to any disclaimer, the term of this patent is extended or adjusted under 35 U.S.C. 154(b) by 135 days.

(21) Appl. No.: 11/615,203

(22) Filed: Dec. 22, 2006

(65) Prior Publication Data

US 2008/0150524 A1 Jun. 26, 2008

(51) Int. Cl.
*G01V 3/00* (2006.01)

(52) U.S. Cl. .................................. 324/319; 324/320

(58) Field of Classification Search ......... 324/300–322; 600/407–422
See application file for complete search history.

(56) References Cited

U.S. PATENT DOCUMENTS

| | | | | |
|---|---|---|---|---|
| 4,301,410 A | * | 11/1981 | Wind et al. | 324/307 |
| 4,673,882 A | * | 6/1987 | Buford | 324/320 |
| 4,675,609 A | * | 6/1987 | Danby et al. | 324/318 |
| 5,023,554 A | * | 6/1991 | Cho et al. | 324/309 |
| 5,412,363 A | * | 5/1995 | Breneman et al. | 335/216 |
| 6,111,409 A | * | 8/2000 | Edwards et al. | 324/303 |
| 6,246,236 B1 | * | 6/2001 | Poitzsch et al. | 324/303 |
| 6,346,813 B1 | * | 2/2002 | Kleinberg | 324/303 |
| 6,479,994 B1 | * | 11/2002 | Hills et al. | 324/306 |
| 6,809,619 B1 | * | 10/2004 | Xu et al. | 335/296 |
| 7,034,537 B2 | * | 4/2006 | Tsuda et al. | 324/320 |
| 7,049,920 B2 | * | 5/2006 | Yoshino et al. | 335/301 |
| 7,112,966 B2 | * | 9/2006 | Motoshiromizu et al. | 324/319 |
| 7,276,908 B2 | * | 10/2007 | Suzuki et al. | 324/318 |
| 2003/0178994 A1 | | 9/2003 | Hurlimann et al. | |

FOREIGN PATENT DOCUMENTS

| | | |
|---|---|---|
| EP | 0730164 A1 | 9/1996 |
| GB | 2336213 A | 10/1999 |
| GB | 2399642 A | 9/2004 |
| WO | 9942852 A1 | 8/1999 |
| WO | 2004088332 A3 | 10/2004 |
| WO | 2007144206 A2 | 12/2007 |

OTHER PUBLICATIONS

Legechenko et al : Journa of Applied Geophysics; vol. 50 pp. 21-46 (2002).*

* cited by examiner

*Primary Examiner*—Brij B Shrivastav
(74) *Attorney, Agent, or Firm*—James McAleenan; Jody Lynn DeStefanis; Dale Gaudier

(57) ABSTRACT

A nuclear magnetic resonance apparatus that may be used in connection with a variety of different tools, including a downhole side-wall coring tool as well as with manufacturing process controllers. In one embodiment, the nuclear magnetic resonance apparatus may include a magnet assembly constructed around a sample chamber. The magnet assembly is constructed and arranged to provide a non-uniform magnetic field having a known magnetic field gradient inside the sample chamber. The use of gradient fields may allow for a more flexible and robust magnet assembly design that may be suitable for a variety of different applications.

23 Claims, 9 Drawing Sheets
(4 of 9 Drawing Sheet(s) Filed in Color)

NUCLEAR MAGNETIC RESONANCE MODULE

BACKGROUND

1. Field of Invention

The present invention relates to nuclear magnetic resonance tools.

2. Discussion of Related Art

Nuclear magnetic resonance (NMR) has become a common wireline logging service and it has been used extensively to estimate properties of rocks (such as porosity, permeability, bound fluid, etc.) and fluids (for example, saturation, viscosity, oil and gas percentage, etc.). NMR measurements, in general, are accomplished by causing the magnetic moments of nuclei ("spins") in a formation to precess about an axis. The axis about which the nuclei precess may be established by applying a strong, polarizing, static magnetic field ($B_0$) to the sample to align the proton spins in a direction parallel to the applied field. Next, a series of radio frequency (RF) pulses are produced so that an oscillating magnetic field $B_1$ is applied to the sample. The static $B_0$ and oscillating $B_1$ fields should be substantially perpendicular to one another. The RF pulse sequence may generally begin with a 90 degree pulse that rotates the magnetization from $B_0$ substantially into the transverse plane. Additional RF pulses, for example, such as 180 degree pulses, may be applied to create a series of spin echoes. One common sequence of RF pulses that may be used is the error-correcting CPMG (Carr-Purcell-Meiboom-Gill) NMR pulse sequence, as discussed for example, in U.S. Pat. No. 6,111,409 to Edwards et al., which is herein incorporated by reference. Techniques of NMR are well known in the literature, as discussed, for example, in U.S. Pat. No. 6,346,813 to Kleinberg, which is herein incorporated by reference.

Reservoir fluids are routinely sampled so that they can be analyzed (e.g., using NMR methods) for their chemical compositions and physical properties in order to facilitate reliable reservoir simulation. Such sampling can be done using probes to extract the fluids by a pressure drawdown provided the mobility (permeability/viscosity) is above the lower limit of such probes. One example of a probe that may be used to extract reservoir fluids is the Schlumberger Modular Formation Dynamics Tester (MDT). Mobility of heavy oil may be very low for reservoirs with low permeability or lower temperatures. Many techniques are being proposed to heat up the formation prior to drawdown in order to reduce the oil viscosity. However, it is uncertain whether any of these strategies will reliably reproduce samples that are identical to the native formation fluids. Furthermore, unconsolidated sand formations may present additional challenges for MDT-type sampling tools.

SUMMARY OF INVENTION

Aspects and embodiments of the invention are directed to a nuclear magnetic resonance (NMR) module that implements magnetic gradient fields to achieve a flexible, low-field and relatively low-cost design. The NMR apparatus may be used in connection with a variety of different tools or systems including, for example, a down-hole side-wall coring tool and various manufacturing process controllers. The magnet assembly may be constructed around a sample chamber such that a sample to be analyzed is contained within the NMR apparatus, allowing for the use of low strength magnetic fields while maintaining a sufficient signal-to-noise ratio for desired NMR measurements such as, for example, diffusion, relaxation time (e.g., longitudinal relaxation time $T_1$ and/or transverse relaxation time $T_2$), chemical shift, and other types of measurements known in the art. As discussed below, the magnet assembly may be constructed to provide a substantially uniform field in one or more directions and also a substantially non-uniform or gradient field in at least one direction. The magnetic field may be controlled through placement of the magnets around the sample chamber and thus, in at least one embodiment, field uniformity may be achieved without requiring specially designed, expensive, uniform magnets. This may allow for a robust and flexible design suitable for use in many different applications.

According to one embodiment, a nuclear magnetic resonance apparatus may comprise a sample chamber, a magnet assembly disposed about the sample chamber and constructed and arranged to provide a non-uniform magnetic field having a known magnetic field gradient inside the sample chamber, a radio frequency (RF) coil positioned so as to substantially surround the sample chamber, and a controller coupled to the RF coil and constructed and arranged to control the RF coil to produce an RF pulse sequence, and an RF power supply constructed and arranged to provide RF power to the RF coil to produce the RF pulse sequence. In one example, the magnet assembly may comprise a first permanent magnet disposed on a first side of the sample chamber, a second permanent magnet disposed on a second side of the sample chamber directly opposite the first permanent magnet, a first pole piece coupled to the first permanent magnet such that the first pole piece is positioned between the first permanent magnet and the sample chamber, and a second pole piece coupled to the second permanent magnet such that the second pole piece is positioned between the sample chamber and the second permanent magnet. In another example, the magnet assembly may further comprise a magnetic shield disposed so as to substantially surround the first and second permanent magnets, the first and second pole pieces and the sample chamber. In one example, the gradient and strength of the non-uniform magnetic field may be controlled by selecting a location and field producing capacity of the first and second permanent magnets. In another example, apparatus may further comprise a pulsed field gradient module. In another example, the apparatus may further comprise a pre-amplifier and a Q-switch, wherein the Q-switch is coupled between the pre-amplifier and the RF power supply and is constructed and arranged to reduce leakage from the RF power supply to the pre-amplifier during transmission of the RF pulse sequence.

Another embodiment of a nuclear magnetic resonance apparatus may comprise an outer magnetic shield, a first permanent magnet disposed within the outer magnetic shield and proximate a first location on an inner surface of the outer magnetic shield, a first pole piece coupled to the first permanent magnet such that the first permanent magnet is located between the outer magnetic shield and the first pole piece, a second pole piece disposed within the outer magnetic shield and proximate a second location on the inner surface of the outer magnetic shield, the second location being directly opposite the first location, a sample chamber disposed within the outer magnetic shield and located centrally between the first and second pole pieces, and a radio frequency coil disposed about the sample chamber, as well as control circuitry coupled to the radio frequency coil and constructed and arranged to control the radio frequency coil to generate a radio frequency pulse sequence, wherein the first permanent magnet is magnetized in a first direction transverse to a longitudinal axis of the sample chamber, such that a magnetic field gradient exists in along an axis perpendicular to the longitudinal axis of the sample chamber. In one example, the first and second pole pieces may each comprise a flat face, the flat faces being oriented toward one another. In another example, the second pole piece may be constructed and arranged to be rotatable such that the flat face of the second pole piece forms an angle with respect to the flat face of the first pole piece so as to create a magnetic field gradient along a second direction, the second direction being perpendicular to both the first direction and the longitudinal axis of the sample chamber. In one example, the outer magnetic shield may be made of iron and the sample chamber may be made of a non-conductive and non-magnetic material, such as plastic. According to one embodiment, the control circuitry may include a Q-switch constructed and arranged to provide damping of pulses of the radio frequency pulse sequence. In one embodiment, the nuclear magnetic resonance apparatus may be integrated with a side-wall coring tool, and the sample chamber may be constructed and arranged to receive a core extracted from a formation by the side-wall coring tool.

According to another embodiment, a method of monitoring a process may comprise acts of providing a nuclear magnetic resonance apparatus having a sample chamber and being constructed and arranged to provide a magnetic field with a known magnetic field gradient inside the sample chamber, directing a series of samples undergoing the process in a continuous stream through the sample chamber without halting the process, and performing a nuclear magnetic resonance measurement on the series of samples to determine at least one properties of the series of samples. In one example, the act of performing the nuclear magnetic resonance measurement may include performing a measurement to detect a presence of water molecules in the series of samples. The series of samples may be, for example, a series of wood samples. In another example, the act performing the nuclear magnetic resonance measurement may include determining a ratio of solid to liquid components in each sample of the series of samples.

According to another embodiment, a down-hole method of analyzing a fluid in an earth formation may comprise acts of providing down-hole a nuclear magnetic resonance apparatus having a sample chamber and being constructed and arranged to provide a magnetic field with a known magnetic field gradient inside the sample chamber, extracting a core from the earth formation, the core containing a sample of the fluid, placing the core inside the sample chamber, and performing down-hole a nuclear magnetic resonance measurement on the core to determine at least one property of the fluid.

BRIEF DESCRIPTION OF THE DRAWINGS

The application file contains at least one drawing executed in color. Copies of this patent or patent application publication with color drawings will be provided by the Office upon request and payment of the necessary fee.

Various aspects and embodiments of the invention are described below with reference to the accompanying figures. In the drawings, which are not intended to be drawn to scale, each identical or nearly identical component that is illustrated in various figures is represented by a like numeral. For purposes of clarity, not every component may be labeled in every drawing. In the drawings.

DETAILED DESCRIPTION

Figure 1:
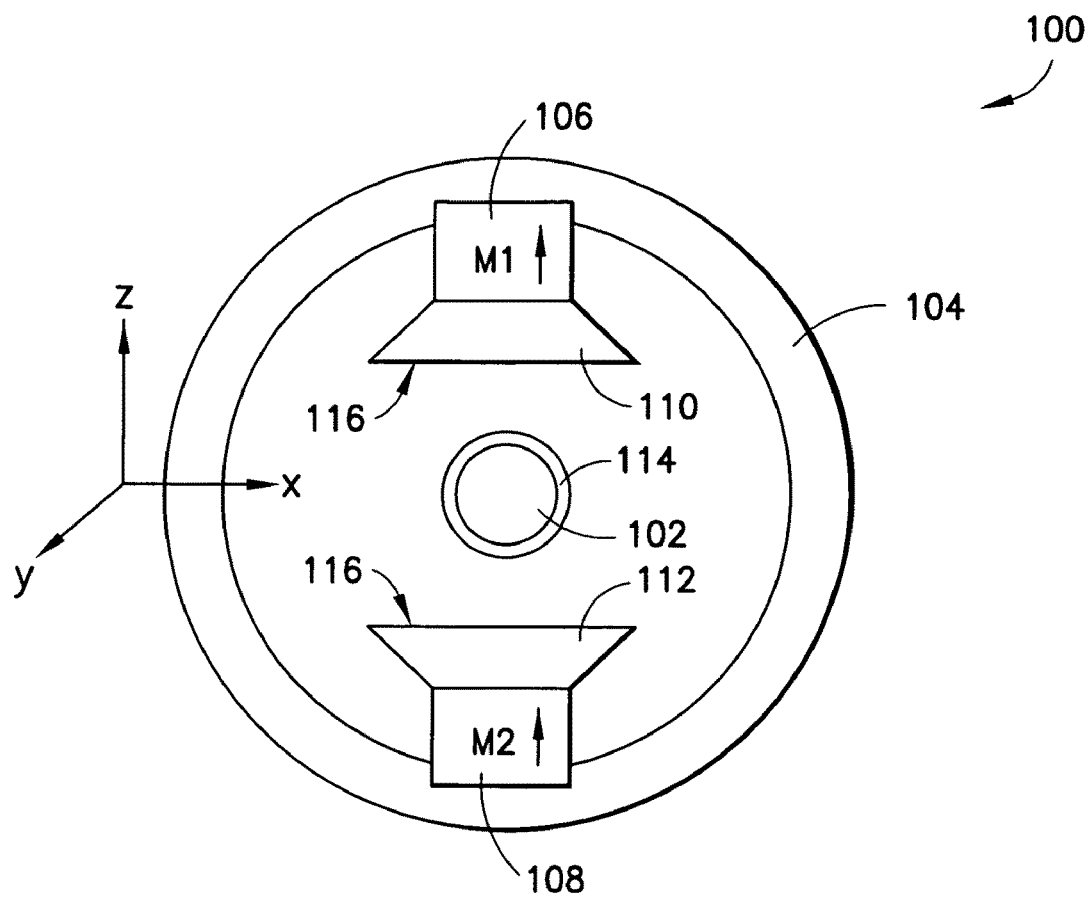
FIG. 1 is a cross-sectional view of one embodiment of an NMR magnet assembly according to the invention.

Embodiments of the invention are directed to a nuclear magnetic resonance apparatus that may be used in connection with a variety of different tools, including a down-hole side-wall coring tool as well as with manufacturing process controllers. Unlike many traditional NMR modules that may be designed around achieving as uniform a magnetic field as possible, embodiments of the NMR apparatus according to the invention may be designed to have an intentionally non-uniform magnetic field in at least one direction. Instead of being substantially uniform, the magnetic field may have a known, and in some embodiments constant, field gradient in one or more directions. The use of gradient fields may allow for a more flexible and inexpensive magnet assembly design, as discussed below.

It is to be appreciated that this invention is not limited in its application to the details of construction and the arrangement of components set forth in the following description or illustrated in the drawings. The invention is capable of other embodiments and of being practiced or of being carried out in various ways. For example, it is to be appreciated that the methods and apparatus described herein are not limited to use in well bores or in connection with well logging, and may be used in a variety of environments and applications. Examples of specific implementations are provided herein for illustrative purposes only and are not intended to be limiting. In particular, acts, elements and features discussed in connection with one embodiment are not intended to be excluded from a similar role in other embodiments. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Side-wall coring is a sampling technique that may involve extracting a sample called a "core" of, for example, a rock formation, and may be accomplished with tools such as the Schlumberger Mechanical Side-wall Coring Tool (MSCT). In the case of well-logging, the core may be extracted from the wall of a well bore, hence the term "side-wall coring." In contrast to traditional sampling methods that extract a sample of fluid from a body (e.g., from a rock formation), the extracted core may include a sample of the body that contains the fluids within it. Side-wall coring may provide a resolution for several of the issues associated with traditional sampling, particularly when combined with in situ measurements such as, for example, NMR measurements performed with embodiments of the apparatus discussed herein. In traditional well bore fluid sampling, accomplished for example by pressure draw-down, the accompanying change in the pressure and/or temperature of the sample may result in dissolution of gases, asphaltene precipitation, and disintegration of weak rocks or unconsolidated sands. By contrast, during a coring process, the native fluids may remain inside the core and the core extraction may be performed without pressure and temperature changes from the conditions of the formation. As a result, there may be minimum damage to the core matrix and the fluids it carries. In addition, cores may be acquired from unconsolidated formations which may present challenges to traditional fluid sampling devices.

According to some embodiments, an NMR module may be incorporated into a side-wall coring tool, such as the Schlumberger MSCT. Side-wall coring tools generally include a core storage area. In one example, an NMR module may be included within the core storage area to provide real-time data on the cores. According to one embodiment, immediately after the core extraction, measurement of the fluids inside the core may be performed using, for example, an NMR module as discussed herein, to determine various characteristics of the fluids such as viscosity, composition, asphaltene concentrations, etc. Such in situ measurements of side-wall cores can be a very useful guide for the coring operation and for comparison with data from NMR wireline logs. In particular, in situ measurements provide the advantage that the data is obtained under the native conditions (e.g., temperature, pressure, fluid composition, wettability, etc.) of the sample.

In one embodiment, the side-wall coring tool may convey acquired cores within a tube inside the tool housing. The cores thus may be cylindrical, for example, approximately 1.5 inches in diameter and approximately 3 inches in length. This may determine the basic geometry of the NMR module magnet assembly. However, it is to be appreciated that the cores may have a different size and need not be cylindrical in shape. The magnet assembly discussed below may therefore be modified, as would be recognized by those skilled in the art, to accommodate cores of different sizes or shapes. Accordingly, such modifications are intended to be part of this disclosure and it is to be appreciated that the invention is not limited to the example magnet assembly geometry illustrated and discussed herein.

Referring to FIG. 1, there is illustrated in cross-section one embodiment of an NMR magnet assembly according to aspects of the invention. The magnet assembly 100 may be constructed around a sample chamber 102 that may receive and contain a core (or other sample) to be analyzed. Conventionally, the sample chamber may be made of metal. However, a metal sample chamber would cause significant signal loss for NMR measurements. Therefore, according to one embodiment, the sample chamber 102 may be made of plastic or another non-conductive, non-magnetic material that may not significantly impede the NMR measurements. In addition, it may be preferable to construct the sample chamber from a material that is also capable of resisting chemical attack by fluids in the sample. The magnet assembly 100 may include a magnetic shield 104, one or more permanent magnets 106, 108, pole pieces 110, 112 and an NMR coil 114. The NMR coil may be connected to NMR electronics (not shown), such as a power supply (146 in FIG. 7) and controller (148 in FIG. 7) that controls the frequency, duration and time spacing of radio frequency (RF) magnetic pulses produced by the coil. The permanent magnets 106, 108 may provide the source of the static magnetic field $B_0$ discussed above. In one example, particularly where the magnet assembly may be used in a down-hole environment, the permanent magnets may comprise a material that has good thermal stability, for example, Samarium Cobalt. The permanent magnets may each be polarized, as shown by an arrow thereon. In one example, the polarization of the permanent magnets may be in a direction perpendicular to the longitudinal axis of the sample chamber. For purposes of illustration, the following discussion may use the x, y, z orientation illustrated in FIG. 1 and may refer to the permanent magnets as being magnetized along the z-direction. However, it is to be appreciated that the illustrated orientation of the x-axis, y-axis and z-axis is arbitrary and the magnets may be oriented and/or magnetized along any direction.

Referring again to FIG. 1, the magnetic shield 104 may provide a return path for the magnetic flux so that the field leakage is small by design. In one example, the magnetic shield 104 may be made of high permeability metal such as, for example, iron or steel. It is to be appreciated that the magnetic shield 104 need not be circular as illustrated, but may have a different shape depending on the shape of and design considerations for any of the sample chamber, the NMR module and the tool with which the NMR module may be used. In addition, the magnetic shield 104 need not be continuous although provision of a continuous shield may help to prevent leakage. The pole pieces 110, 112 may be made of a high magnetic permeability material, such as iron or steel. The pole pieces 110, 112 may be attached to an inner face of each permanent magnet 106, 108, as shown in FIG. 1. The width of the faces 116 of the pole pieces may be selected so as to control the magnetic field strength in the center of the magnet assembly, in this case, in the center of the sample chamber 102. In addition, in one embodiment, the shape of the pole pieces 110, 112 may be designed to optimize the magnetic field uniformity along the x and y directions. Although two permanent magnets and two pole pieces are illustrated in FIG. 1, it is to be appreciated that the invention is not so limited and the magnet assembly 100 may include more than two or fewer than two permanent magnets and pole pieces, depending on the geometry of the sample chamber and the overall magnet assembly.

According to one embodiment, the placement of the permanent magnet(s) may determine primarily the magnetic field in the sample chamber and the field gradient. For example, if equal amount of permanent magnet is placed opposite sides of the sample chamber, such that M1=M2 (M1 being the magnetic field strength produced by permanent magnet(s) 110 and M2 being the magnetic field strength produced by permanent magnet(s) 112), then the magnetic field in the center of the apparatus (in the center of the sample chamber in the illustrated example) may be relatively uniform and the gradient along the z-direction may be at a minimum. By contrast, when there is an imbalance in the magnetic field produced on either side, the field gradient along the z-direction may increase. However, if the total amount of permanent magnet remains the same (e.g., M1 is increased, but M2 is decreased by an equal amount, such that M1+M2 remains the same), the magnetic field strength in the center may remain approximately unchanged. It is to be appreciated that the phrase "amount of permanent magnet" as used herein is intended to refer to the magnetic field producing capability of the material rather than a volumetric amount of actual material. In other words, a small volume of a highly magnetic material may produce a high-strength magnetic field and is therefore referred to as a large amount of permanent magnet (even though the actual volume may be small). By contrast a large volume of a weakly magnetic material may produce only a small field and is thus referred to as a small amount of permanent magnet.

The above-discussed design principle may allow more flexible and independent variation of magnetic field strength and the magnetic field gradient. In particular, a substantially uniform magnetic field may be achieved in at least one direction through appropriate placement of the permanent magnets and without requiring that the magnetic field produced by any one magnet be very uniform. In addition, the magnet assembly may be constructed to have an intentionally non-uniform field, and instead provide a magnetic field with a known, an in some embodiments constant, field gradient. These principles may substantially reduce the cost of the apparatus compared with traditional systems that attempt to achieve as uniform a magnetic field as possible. Furthermore, because the magnet assembly may be designed and constructed around the sample chamber, the sample may be entirely contained within the apparatus, resulting in an improved signal-to-noise ratio. Thus, a relatively low magnetic field strength may be used while still obtaining a sufficient signal-to-noise ratio for desired measurements. This may also increase the flexibility and usefulness of the apparatus as high-field systems may be costly, bulky and dangerous for many applications.

The magnetic field design may also be flexible in allowing creation of magnetic field gradients in directions other than the z-direction by appropriately arranging the permanent magnets, rotating the faces of the pole pieces, and adjusting the relative sizes of the pole pieces. For example, to produce a gradient along the axial (y) direction, an equal amount of permanent magnet may be can be placed on opposite sides of the sample chamber (e.g., in the positions illustrated in FIG. 1 for permanent magnets 106 and 108) and the amount of permanent magnet may be progressively reduced along the y direction. In another example, an x gradient may be produced by tilting one of the pole pieces, as illustrated, for example, in FIG. 2 and discussed in more detail below.

Figure 2:
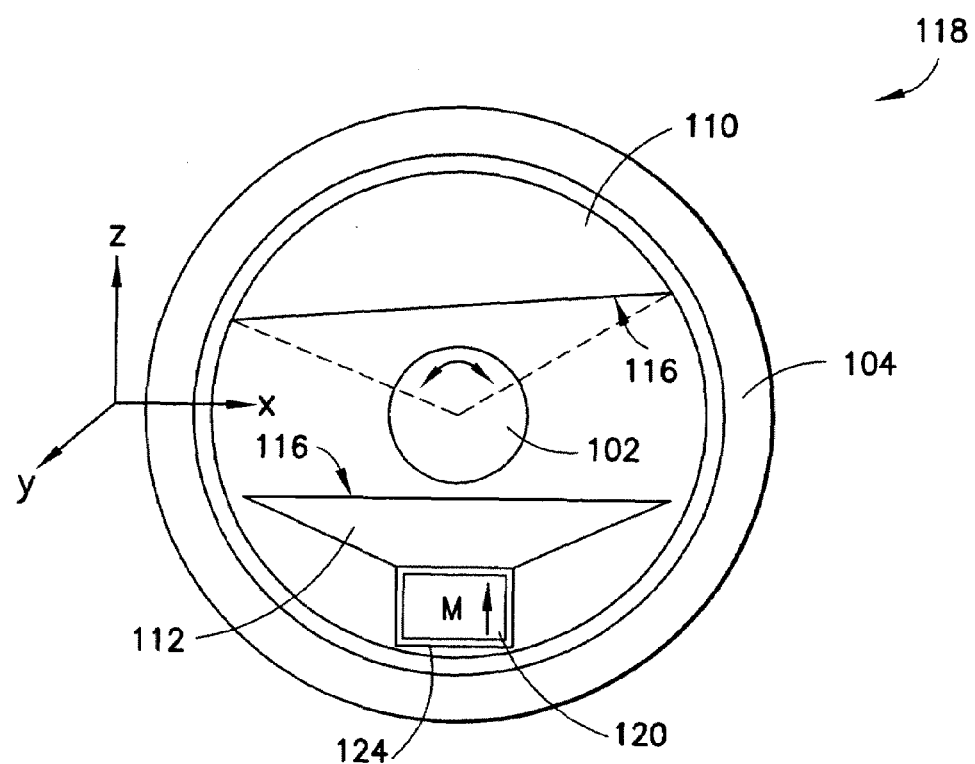
FIG. 2 is a cross-sectional view of another embodiment of an NMR magnet assembly according to the invention.

Referring to FIG. 2, there is illustrated in cross-section another embodiment of an NMR magnet assembly 118 according to the invention. In this embodiment, the permanent magnet(s) 120 may be installed on one side of the assembly, as illustrated. Thus, the magnetic field gradient along the z-direction may be maximum. The magnet assembly 118 may again include two pole pieces 110, 112 with flat pole faces 116 and an outer magnetic shield 104. In one example, the pole pieces 110, 112 and the shield may be of iron with high magnetic permeability in order to channel the magnetic flux. In this embodiment, the top pole piece 110 was made to allow rotation, as indicated by the dotted lines. In one example, the degree of allowable rotation may be about 20 degrees in either direction (clockwise or anticlockwise) from a neutral position in which the pole face 116 is horizontal. However, it is to be appreciated that many other designs are also possible. The rotation of the pole piece 110 may be used to create a component of the field gradient along the x-direction, as discussed above.

To illustrate performance of a magnet assembly according to the invention, an embodiment of the magnet assembly of FIG. 2 was constructed and tested. In this example, the pole pieces 110, 112 and the shield 104 were made of iron. The pole face 116 was approximately 6.2 inches across in the x-direction. The shield had an outer diameter of about 8.9 inches with a thickness of about 0.5 inches, giving an inner diameter of about 7.9 inches. The length of the magnet assembly (in the y-direction) was about 6 inches. For easy handling, the permanent magnets 102 were encased in an Aluminum frame 124 and bolted to the pole piece 112 and to the shield 104. The permanent magnets 120 were placed in between the pole piece 112 and the shield 104, as illustrated in FIG. 2. The Aluminum frame was approximately 1.1 inches in the z-direction by about 1.6 inches in the x-direction. The permanent magnets were made of an alloy of Neodymium, iron and Boron (Nd—Fe—B), and are herein referred to as "Nd magnets." Since the magnetic parts can exert significant force between them, a non-magnetic mounting system was designed to guide the insertion of the lower subassembly (including the permanent magnets 120, frame 124 and the pole piece 112) into the shield 104.

Figure 3A:
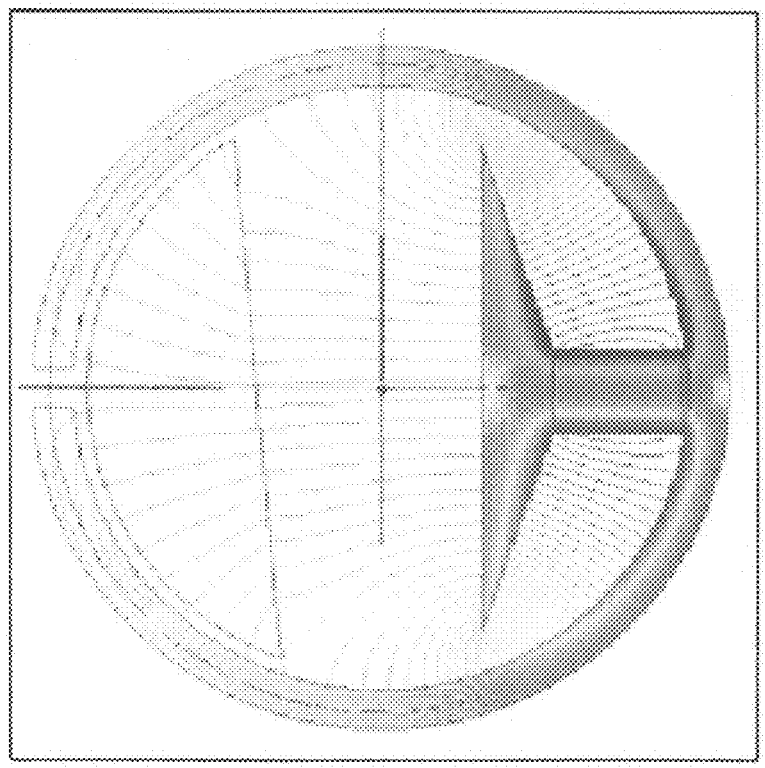
FIG. 3A is a numerical simulation of the magnetic flux produced by the magnet assembly of FIG. 2.
Figure 3A:
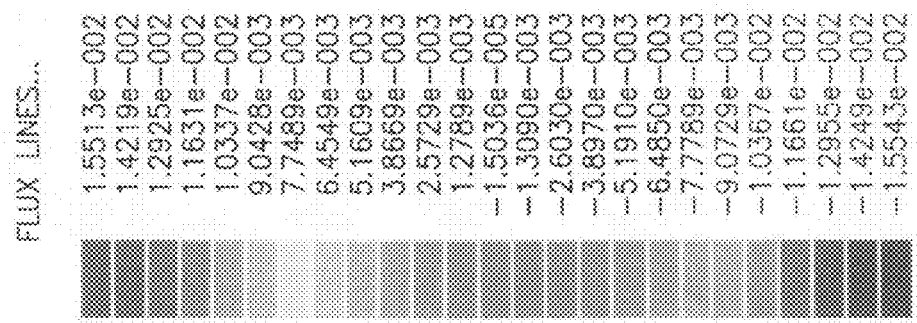
Figure 3B:
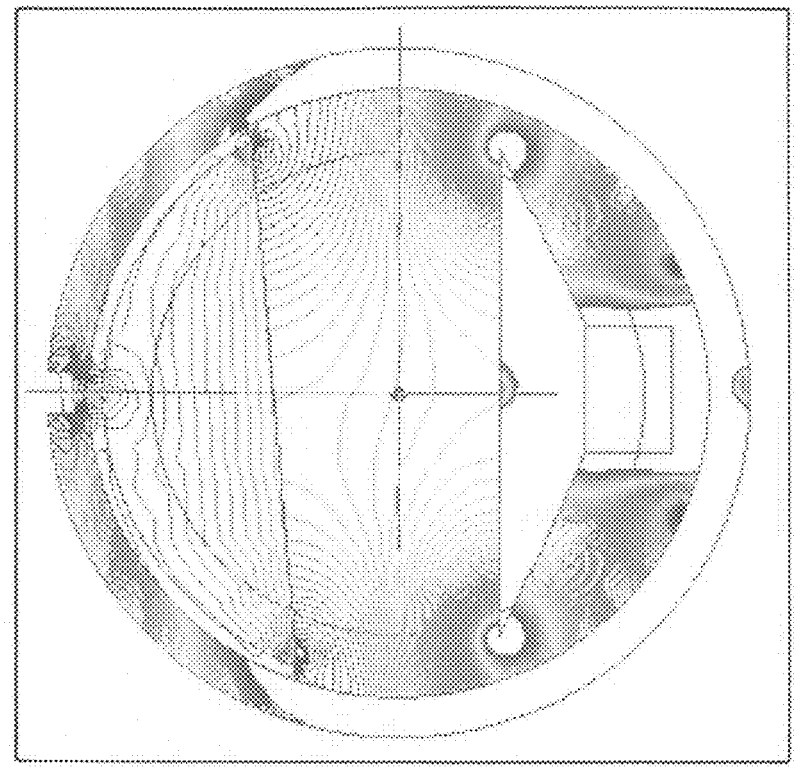
FIG. 3B is a numerical simulation of the magnetic field produced by the magnet assembly of FIG. 2.
Figure 3B:
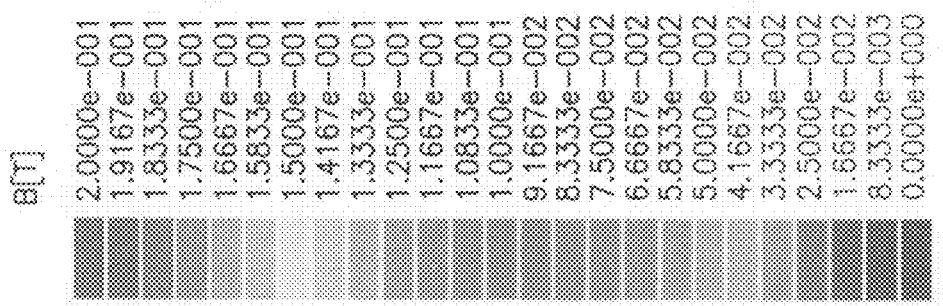

Referring to FIGS. 3A and 3B, there is illustrated the results of a numerical calculation of the magnetic flux (FIG. 3A) and magnetic field (FIG. 3B) generated by the above-described example magnet assembly 118. A predominant gradient along the z-direction may be observed. The magnetic field in the center region was scanned using a Hall-effect probe and a three-axis scanner, as known to those skilled in the art. In the central region of the magnet assembly, the magnetic field was observed to be substantially uniform in the x-y plane with a field strength of approximately 280 Gauss. When the top pole piece 110 was rotated, a significant field gradient was observed along the x-direction.

According to one embodiment, temperature regulation may be included in the magnet assembly to improve field stability. However, because of the gradient design (i.e., the magnet assembly may be intentionally designed to have a known field gradient), e.g., for the magnet assembly of FIG. 2, a change in temperature will merely shift the region of the resonance slightly. For an Nd magnet with a temperature coefficient of 0.1% per degree, a temperature change of 5 degrees Celsius may correspond to a position shift of about 0.1 to about 0.2 centimeters (cm), which generally may be much smaller than the size of the sample. Therefore, for at least some embodiments, temperature regulation may not be needed.

As discussed above, an NMR apparatus according to embodiments of the invention may also include an RF NMR coil 114 (see FIG. 1) and associated NMR control circuitry (not shown). In one embodiment, the RF coil may be a solenoid coil wound on, for example, a Teflon form. As shown in FIG. 1, the RF coil may be placed in or near the center of the magnet assembly 100. The control circuitry may include a tuning circuit to tune the RF resonance frequency of the RF coil. As discussed above, to perform NMR measurements, the RF coil may be tuned to the Lamor frequency of nuclei of interest. The RF coil may be controlled by the control circuitry to produce an RF pulse sequence, such as, for example a CPMG sequence to perform NMR measurements. In one embodiment, the NMR control circuitry may include an NMR console such as, for example, the Apollo console available from Tecmag, TX. The console may run NMR processing software, such as NTNMR software that is supplied by Tecmag and integrated with the Apollo console. In addition, an RF power amplifier may be included, as well as a signal preamplifier. One example of a suitable signal preamplifier is available from Miteq, having part number AU-1579. In one embodiment, the NMR apparatus may also include a pulse field gradient module 144 (see FIG. 7) to allow pulsed field gradient measurements on the sample, as known to those skilled in the art. The electronics controller may also be coupled to the pulsed field gradient module to control the strength and spacing of the pulses.

Figure 6:
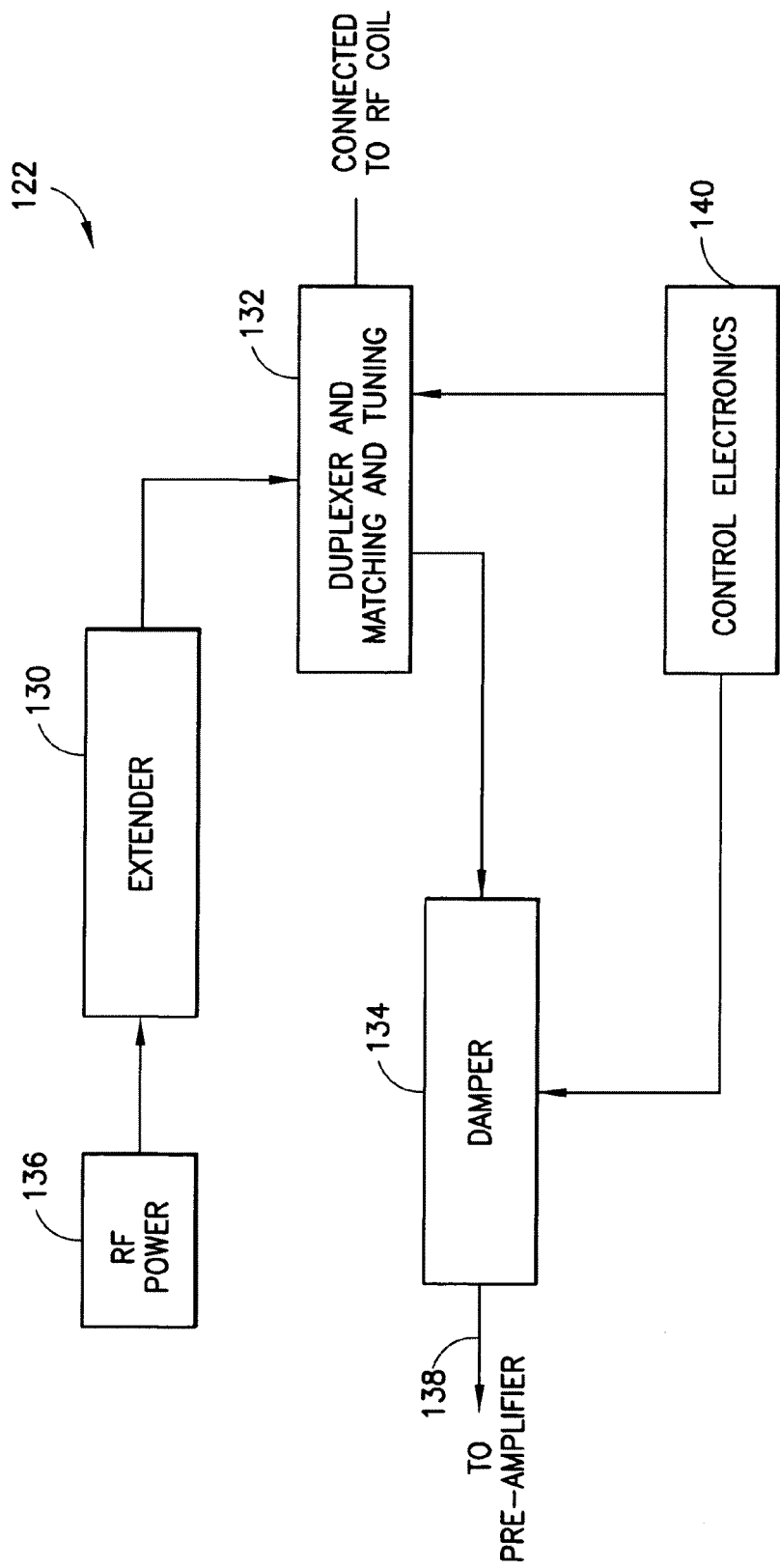
FIG. 6 is a block diagram of a Q-switch according to an embodiment of the invention.

According to one embodiment, the tuning circuit may be integrated with a Q-switch, as illustrated in FIG. 6. The Q-switch 122 may allow rapid damping of the ringdown of the RF pulses by providing a critically-damped current path. In the illustrated embodiment, the Q-switch includes an extender 130 coupled between the source of RF power 136 and the electronics. The extender 130 may allow a high power RF signal (such as the RF pulses) to pass, but may block low level RF signals (such as the detected NMR signals). The Q-switch may further comprise a damper 134 that may act to further reduce leakage of RF power during the RF pulses. A duplexer 132 may allow a high power RF signal from the RF source 136 to be transmitted to the RF coil (to produce the RF pulses) and, when the high power RF is off, to allow low level NMR signals to be passed (through the damper) to the preamplifier, as indicated by line 138. In one example, the duplexer may use a TTL pulse through the use of FETs as switches to turn the damper 132 on and off. Digital control electronics 140 may be provided to control operation of the duplexer and the damper. In one example, the use of such a Q-switch may greatly reduce the dead time of the reception of spin-echoes to about 50 micro-seconds after the 180 degree pulse.

Figure 4:
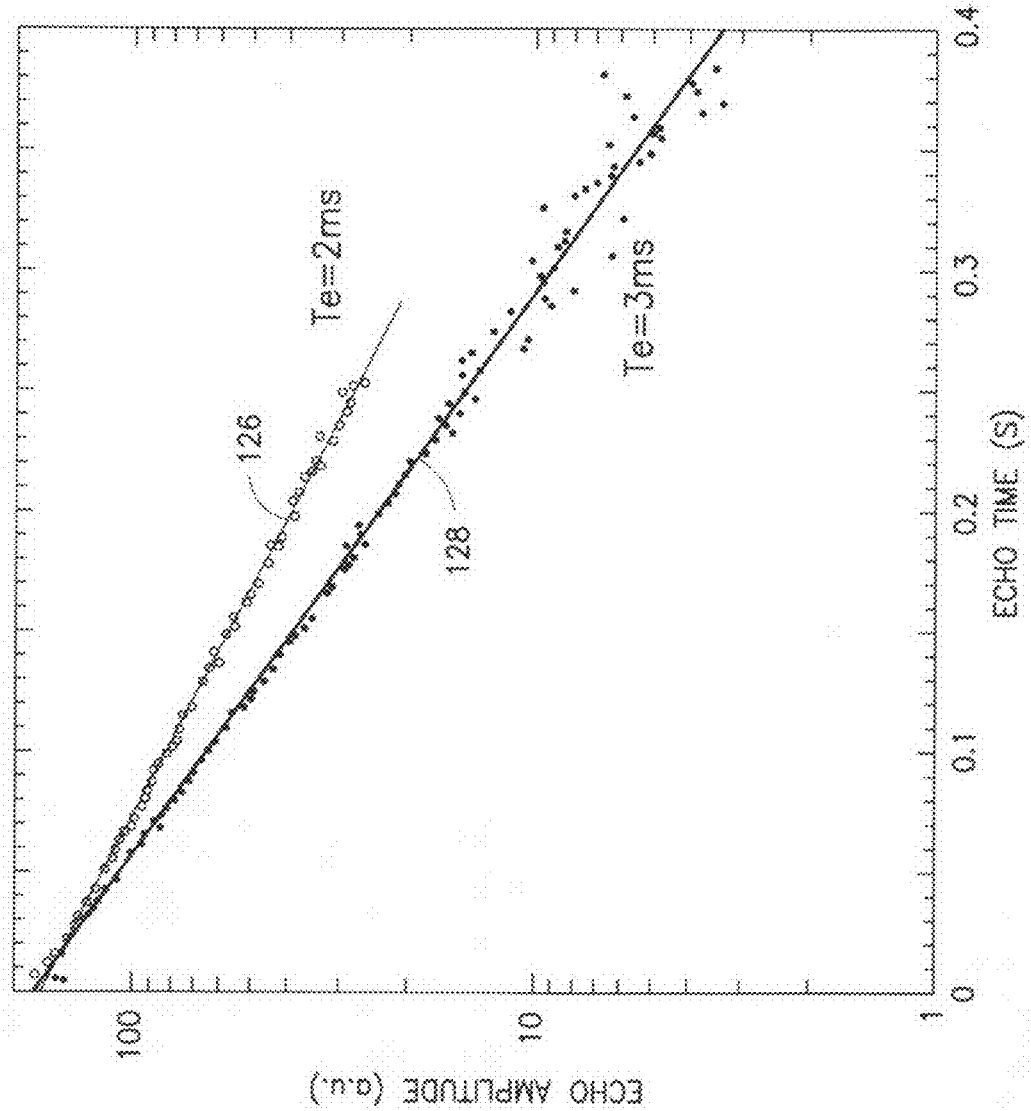
FIG. 4 is a plot of echo amplitude versus echo time for examples performed on a water sample using an NMR apparatus according to an embodiment of the invention.

A CPMG example performed on a water sample using the NMR module according to embodiments of the invention. For this example, the RF power amplifier was a 50 Watt amplifier. The length of the RF solenoid coil was approximately 2 inches and the coil had a diameter of about 2 inches. The resonance frequency was 1.16 Megahertz (MHz). The temperature was about 25 degrees Celsius. A matched filter was used to extract the echo amplitude. Two different echo spacing times, $T_e$, were used. In the first example, the echo spacing was $T_{e1}$=2 milliseconds (ms). In the second example, the echo spacing was $T_{e2}$=3 ms. Referring to FIG. 4, there is illustrated a plot of echo amplitude versus echo time (in seconds) for the two examples. Line 126 represents the data from the first example, and line 128 represents the data from the second example. The signal decay showed a single exponential behavior due to both spin-spin relaxation and diffusion in the gradient field. Equation (1) below describes the $T_e$ dependence of the measured signal decay rate.

$$\frac{1}{T_2} = \frac{1}{T_{2b}} + \frac{1}{12} D(\gamma G) T_e^2 \quad (1)$$

where: $T_2$ is the transverse (spin-spin) relaxation time;
$T_{2b}$=0.206 seconds for the water sample;
G is the field gradient;
$\gamma$ is the gyromagnetic ratio of the nuclei; and
D is the diffusion coefficient.

The difference of $1/T_2$ for the two examples with different $T_e$ will allow direct measurement of the diffusion contribution:

$$\Delta\left(\frac{1}{T_2}\right) = \frac{1}{12} D(\gamma G)^2 (T_{e1}^2 - T_{e2}^2) \quad (2)$$

Thus, using equation (2) and the data in FIG. 4, the field gradient in the magnet may be determined. In this example, the field gradient was determined to be about 20.4 Gauss per centimeter near the center of the magnet assembly.

Embodiments of an NMR apparatus according to the invention may be used for a variety of applications. As discussed above, one such application is in the field of well logging, where the NMR apparatus may be used in conjunction with a side-wall coring tool. An advantage of an NMR apparatus according to embodiments of the invention compared to wireline logging is that the sample may be within the NMR instrument so that the measurement may be very efficient and of much higher quality. Furthermore, because the signal-to-noise ratio is higher (due to the far better filling factor when the sample is within the NMR magnet assembly versus outside of the NMR magnet assembly), the NMR apparatus according to embodiments of the invention may allow more rapid pulsing and acquisition of NMR signals. This may be particularly important to characterize heavy oils. Another advantage offered by the NMR apparatus of the invention is that the gradient magnetic field may be used in combination with properly designed RF pulses to select only a portion of the sample for examination, similar to the slice selection used in medical magnetic resonance imaging (MRI). This may allow measurement of the properties of samples within a selected volume. By changing the frequency of the RF pulses, the selected volume may be moved around the sample, thereby creating an image of the sample properties. This image may be used to examine, for example, heterogeneity of a rock matrix and/or the fluids inside. For example, the fluid composition in core taken from a rock formation may be affected by the invasion of the drilling mud, causing a gradient of fluid properties and composition transverse to the direction of the borehole.

These and other characteristics of the core may be measured using the NMR apparatus in combination with the side-wall coring tool. In particular, such a system may be able to fully examine the fluids in the rock without extracting the fluids from the rock. Rather, as discussed above, a core of rock with the fluids contained therein may be extracted from a formation and analyzed in situ. This may be important in heavy oil formations where MDT-type testing may not be able to withdraw fluids properly due to their low mobility. Thus, an NMR module according to embodiments of the invention may be able to provide better measurements compared to wireline logging, especially for heavy oils, because with the system of the invention, the fluids may be analyzed in their native conditions.

Figure 5A:
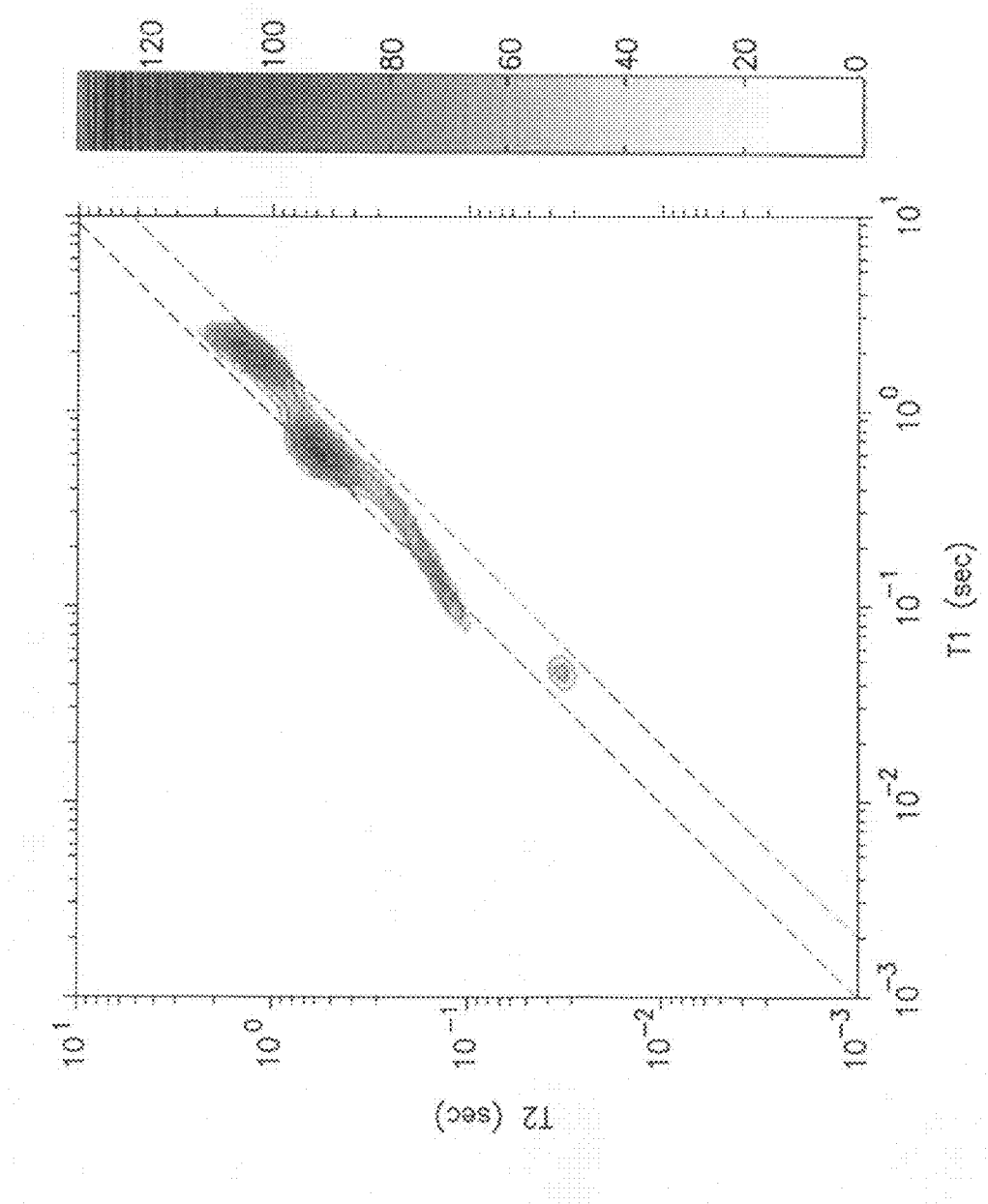
FIG. 5A is a two-dimensional $T_1$-$T_2$ map obtained from NMR measurements of a crude oil sample using an NMR apparatus according to an embodiment of the invention.
Figure 5B:
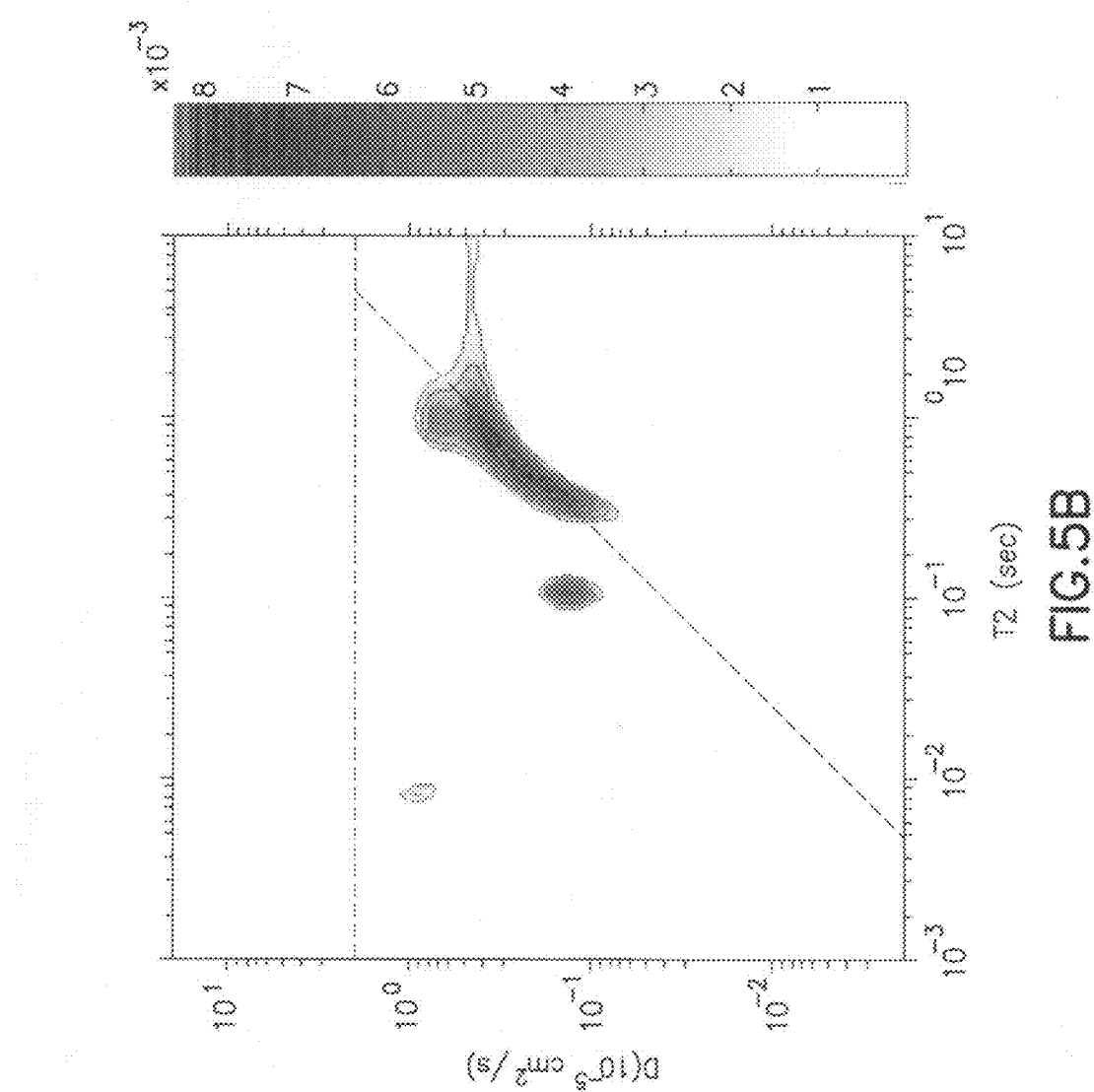
FIG. 5B is a two-dimensional D-$T_2$ map obtained from NMR measurements of the crude oil sample using the NMR apparatus according to an embodiment of the invention.

Another example was performed to illustrate the applicability of an embodiment of the NMR apparatus for two-dimensional (2-D) NMR measurements. In this example, two 2-D measurements were performed on crude oil samples. The first was a $T_1$-$T_2$ correlation measurement and the second was a D-$T_2$ correlation measurement. The details of these measurements are known to those skilled in the art and well described in the literature. For the $T_1$-$T_2$ example, an inversion-recovery CPMG pulse sequence was used and 1024 echoes were acquired for 36 different recovery times. For the D-$T_2$ example, a stimulated echo-CPMG sequence was used with 124 echoes acquired for 64 different encoding steps. A two-dimensional Laplace inversion algorithm (FLI) was used to obtain the two-dimensional maps illustrated in FIGS. 5A and 5B. FIG. 5A illustrates the $T_1$-$T_2$ map and FIG. 5B illustrates the D-$T_2$ map. The data demonstrates the capacity of the NMR apparatus for 2-D NMR measurements.

According to one embodiment, several magnet assemblies with different characteristics of the magnet may be installed in a tool for serial or parallel measurements of different properties of samples. For example, magnet assemblies may be designed to have field gradients along different directions in order to obtain profiles (or one-dimensional images) of the sample properties (such as fluid composition) along multiple directions, e.g. along the core axis and transverse to the core axis. In another example, multiple RF coils may be included near the sample chamber to provide pulsed field gradients or pseudo-static field gradients. These gradients may be used, for example, for imaging of the sample, measurement of molecular diffusion, measurement of fluid movement inside the sample, determination of pore sizes, and determination of the surface-to-volume ratio of the rock.

Furthermore, a side-wall coring tool with an integrated NMR module may be used to monitor changes in the sample (such as changes in fluid composition and profiles, etc.) as the sample conditions are changed. For example, the system may be used to monitor the sample as changes are made in the pressure and/or temperature of the sample in order to probe the thermodynamic and phase properties of the fluids. In one example, such changes in the conditions of the sample may be brought about by admitting or evacuating gas or fluid into the sample, or by heating or cooling the sample. In another example, further changes in the sample conditions may be induced by addition of fluids to the sample to cause spontaneous imbibition, drainage, or other displacement of the fluids originally inside the sample. These and other changes may be performed to simulate the reservoir conditions during various production scenarios, such as, for example, pressure drawdown, water flood, carbon-dioxide flood, and other techniques used for enhanced oil recovery from reservoirs. In one example, for experiments in which fluids or gases are forced to invade the sample, it may be very important to measure the spatial profile of the invasion, for both the native fluid and the displacement fluids. In addition, it may be useful to compare the composition of fluids being extracted from a reservoir with the composition of fluids in an original core both before and after changes to the core conditions are made. Such tests may be used to evaluate different extraction strategies directly under native reservoir conditions for both the rock matrix and fluids.

As discussed above, an NMR apparatus according to the invention may also be used in variety of applications outside of the oil field industry. For example, many manufacturing processes may involve moving the processing materials through a system in a continuous stream. In these circumstances, it may be ideal to insert analytical instrumentation inline with the production stream in order to perform non-invasive measurements for process and quality control. For example, in a chemical process, different molecules may be produced at different stages of the manufacturing system. It may be extremely useful to determine the composition of the stream continuously and to have the measured data be integrated with the process control system in order to optimize or improve the process. Furthermore, in food processing, it may important to examine continuously the raw material and the final product, for example, to monitor its moisture, fat and/or sugar content.

NMR spectroscopy and the associated equipment may be ubiquitous in chemical, biological and material research, and may be being used for analysis as a batch-mode process. However, because of the bulky size, cost and complexity of operation and maintenance, traditional high-field systems may not be very useful, robust, or cost-effective as a process-control system. In particular, it may be difficult and/or costly to integrate traditional systems into a production line. In addition, the high magnetic field used in such systems may also present a hazard to the environment. By contrast, a low field NMR system may be much more flexible, relatively inexpensive, and may be customizable for inline analysis. According to one embodiment, an NMR module according to the invention may be a low field device. A drawback of traditional low field NMR devices is the lower signal to noise ratio. The NMR apparatus of the invention may circumvent this problem in two ways. Firstly, because the sample may be contained entirely within the NMR apparatus, the filling factor may be very good which in turn may facilitate a good signal-to-noise ratio. Second, the sample chamber may be designed so as to accommodate larger samples, providing more volume and thus more nuclei to contribute to the NMR signal, thereby raising the signal-to-noise ratio.

One technical issue that is quite relevant in comparing different NMR equipment is that of field uniformity. Most of NMR theory and equipment are designed around a very uniform magnetic field. This high field uniformity is to a large degree the cause of the high price of traditional NMR systems. By contrast, the NMR apparatus according to embodiments of the invention may use a magnet assembly that is designed to be non-uniform with a constant field gradient. The reduced uniformity requirement simplifies the magnet design and may reduce its cost. In addition, the use of a gradient field may allow a robust operation of the system with regard to temperature shift and certain types of drift of electronics. Thus, an NMR apparatus according to embodiments of the invention may be very suitable to provide inline (as the process stream may be directed through the sample chamber) and non-invasive measurements. The magnet assembly may be easily designed around an existing process line and measurements may be taken without disrupting manufacturing.

NMR is known to show dramatic different characteristics for solids and liquids. For example, the proton-proton spin interaction is much stronger in a solid than in a liquid, resulting in a rapid signal decay for the solid portion of a sample and a much slower decay for the liquid portion of the sample. As a result, the signal from a mixture of solid and liquid materials is expected to be approximately the sum of two components, with rapid and slow decay time constants, respectively. For example, a signal from a sample containing both liquid and solid components may be described by the following equation:

$$S(t) = A\exp\left(-\frac{t}{T_f}\right) + B\exp\left(-\frac{t}{T_s}\right) \quad (3)$$

where: t is measurement time;
$1/T_f$ is the fast time constant;
$1/T_s$ is the slow time constant; and
A and B are proportional to the amount of material in the solid phase and the liquid phase, respectively.

An NMR measurement may measure S(t) for a series of values of t. From equation (3), and analysis of the data, all four parameter may be determined. Thus, the composition of the sample (e.g., ratio of solid to liquid) may be determined. This type of measurement may be useful for chemical and/or food processing manufacturing in which a product may change from containing more liquid to more solid, or vice versa, during the manufacturing process. Thus, an NMR module may be used to monitor progression of the process and, if integrated with the process control electronics, may be used to start and/or stop various steps of the process.

Another application in which the NMR apparatus of the invention may be very useful is that of wood drying. Living wood contains a very high percentage of water. Therefore, after trees are cut for lumber, the wood generally must be dried before it becomes usable for building materials, furniture, cabinetry etc. The wood is generally dried by moving through large ovens. Traditionally, a piece of wood may be removed from the oven to be examined to determine whether it is sufficiently dry. However, this method may be very inefficient as the drying process may be halted to remove the wood from the oven and also, because the wood pieces may be of different sizes, some may be dry while others are not. An NMR apparatus according to embodiments of the invention may be designed around an existing wood drying process line (e.g., such that at least some of the wood may pass through the sample chamber) and may be used to monitor the dryness of the wood without interrupting the drying process. Specifically, the NMR apparatus may be configured to detect water molecules (e.g., by diffusion or chemical shift measurements, as known to those skilled in the art) and thus, provide an indication of the dryness of the wood.

Figure 7:
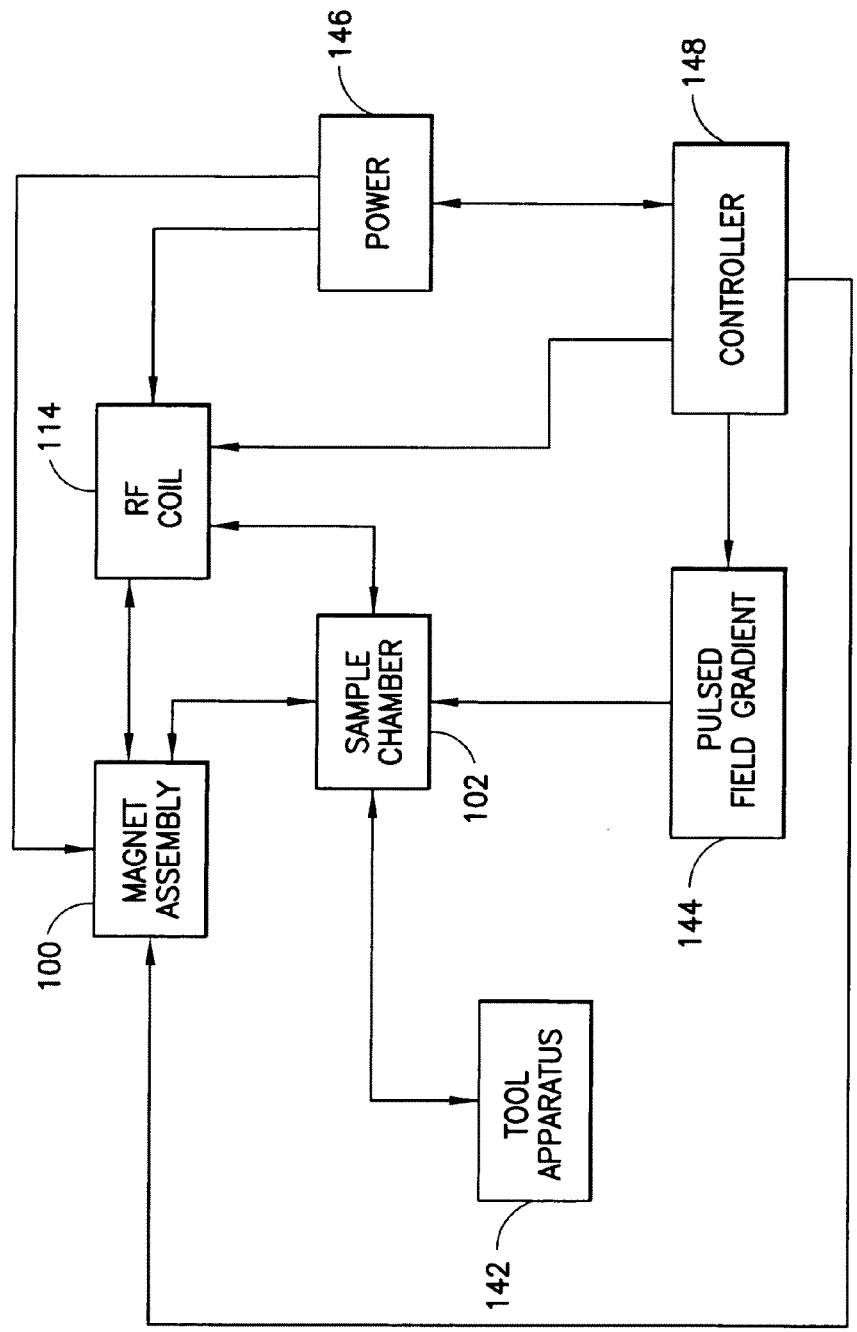
FIG. 7 is a block diagram of an NMR apparatus according to an embodiment of the invention.

In summary, aspects and embodiments of the invention are directed to an NMR apparatus or module that may be used in many different applications. A general block diagram of an NMR apparatus is shown in FIG. 7. The magnet assembly of the NMR module may be constructed around a sample chamber, thus providing for the sample to be entirely contained within the NMR apparatus with the resulting advantages of good filling factor, good signal-to-noise ratio and accompanying possibility of using low-strength magnetic fields. The placement of the permanent magnet and pole pieces may be controlled so as to produce magnetic fields in the sample chamber that have a known gradient in one or more directions, allowing for a flexible and possibly low cost design. In at least one embodiment, the NMR apparatus may be incorporated in a down-hole side-wall coring tool, allowing in situ measurements of formation fluids in the natural conditions. In addition, embodiments of the apparatus may be constructed around existing manufacturing or other process lines to provide non-invasive, in situ monitoring of a variety of processes. A tool apparatus is represented in FIG. 7 by block 142. Furthermore, the apparatus may be calibrated (e.g., by performing a measurement on a sample having a known composition, such as a water sample) once installed in either the tool or process line, such that the operating field gradients may be well known and can be accounted for in the processing of data acquired by the apparatus. In one embodiment, the NMR apparatus may also include an optional pulse field gradient module 144 to allow pulsed field gradient measurements on the sample.

Having thus described various aspects of at least one embodiment, it is to be appreciated that the invention is not limited to the specific examples described herein and that the principles of the invention may be applied to a wide variety applications. The above description is therefore by way of example only, and includes any modifications and improvements that may be apparent to one of skill in the art. The scope of the invention should be determined from proper construction of the appended claims and their equivalents.

What is claimed is:

1. A nuclear magnetic resonance apparatus comprising:
   a sample chamber; and
   a magnet assembly disposed about the sample chamber and constructed and arranged to provide a substantially non-uniform magnetic field having a known magnetic field gradient inside an approximate center of the sample chamber such that the substantially non-uniform magnetic field is controlled through one of a placement of at least one magnet or by one or more component;
   a radio frequency (RF) coil positioned so as to substantially surround the sample chamber;
   a controller coupled to the RF coil and constructed and arranged to control the RF coil to produce a RF pulse sequence; and
   an RF power supply constructed an arranged to provide RF power to the RF coil to produce the RF pulse sequence.

2. The nuclear magnetic resonance apparatus as claimed in claim 1, wherein the magnet assembly comprises:
   a first permanent magnet disposed on a first side of the sample chamber;
   a second permanent magnet disposed on a second side of the sample chamber directly opposite the first permanent magnet;
   a first pole piece coupled to the first permanent magnet such that the first pole piece is positioned between the first permanent magnet and the sample chamber; and
   a second pole piece coupled to the second permanent magnet such that the second pole piece is positioned between the sample chamber and the second permanent magnet.

3. The nuclear magnetic resonance apparatus as claimed in claim 2, wherein the magnet assembly further comprises a magnetic shield disposed so as to substantially surround the first and second permanent magnets, the first and second pole pieces and the sample chamber.

4. The nuclear magnetic resonance apparatus as claimed in claim 2, further comprising a pulsed field gradient module; and wherein the controller is further coupled to the pulsed field gradient module.

5. The nuclear magnetic resonance apparatus as claimed in claim 2, wherein a location and field producing capacity of the first and second permanent magnets are selected so as to produce inside the sample chamber the non-uniform magnetic field with the known magnetic field gradient in at least one direction.

6. The nuclear magnetic resonance apparatus as claimed in claim 2, further comprising a pre-amplifier and a Q-switch;
   wherein the Q-switch is coupled between the pre-amplifier and the RF power supply and is constructed and arranged to reduce leakage from the RF power supply to the pre-amplifier during transmission of the RF pulse sequence.

7. A nuclear magnetic resonance apparatus comprising:
   an outer magnetic shield;
   a first permanent magnet disposed within the outer magnetic shield and proximate a first location on an inner surface of the outer magnetic shield;
   a first pole piece coupled to the first permanent magnet such that the first permanent magnet is located between the outer magnetic shield and the first pole piece;
   a second pole piece disposed within the outer magnetic shield and proximate a second location on the inner surface of the outer magnetic shield, the second location being directly opposite the first location;
   a sample chamber disposed within the outer magnetic shield and located centrally between the first and second pole pieces;
   a radio frequency coil disposed about the sample chamber; and
   control circuitry coupled to the radio frequency coil and constructed and arranged to control the radio frequency coil to generate a radio frequency pulse sequence,
   wherein the first permanent magnet is magnetized in a first direction transverse to a longitudinal axis of the sample chamber, such that a magnetic field gradient exists in along an axis perpendicular to the longitudinal axis of the sample chamber.

8. The nuclear magnetic resonance apparatus as claimed in claim 7, wherein the first and second pole pieces each comprise a flat face, the flat faces being oriented toward one another.

9. The nuclear magnetic resonance apparatus as claimed in claim 8, wherein the second pole piece is constructed and arranged to be rotatable such that the flat face of the second pole piece forms an angle with respect to the flat face of the first pole piece so as to create a magnetic field gradient along a second direction, the second direction being perpendicular to both the first direction and the longitudinal axis of the sample chamber.

10. The nuclear magnetic resonance apparatus as claimed in claim 7, wherein the outer magnetic shield comprises iron.

11. The nuclear magnetic resonance apparatus as claimed in claim 7, further comprising a pulsed field gradient module coupled to the control circuitry.

12. The nuclear magnetic resonance apparatus as claimed in claim 7, further comprising a radio frequency power supply coupled to the radio frequency coil to produce the radio frequency pulse sequence.

13. The nuclear magnetic resonance apparatus as claimed in claim 12, wherein the control circuitry comprises a Q-switch constructed and arranged to reduce leakage from the radio frequency power supply during transmission of the radio frequency pulse sequence.

14. The nuclear magnetic resonance apparatus as claimed in claim 7, wherein the apparatus is integrated with a side-wall coring tool, and wherein the sample chamber is constructed and arranged to receive a core extracted from a formation by the side-wall coring tool.

15. The nuclear magnetic resonance apparatus as claimed in claim 7, wherein the sample chamber comprises a non-conductive and non-magnetic material.

16. The nuclear magnetic resonance apparatus as claimed in claim 15, wherein the sample chamber comprises a plastic material.

17. A method of monitoring a process, the method comprising:
providing a nuclear magnetic resonance apparatus having a sample chamber and a magnet assembly disposed about the sample chamber and constructed and arranged to provide a substantially non-uniform magnetic field having a known magnetic field gradient inside an approximate center of the sample chamber such that the substantially non-uniform magnetic field is controlled through one of a placement of at least one magnet or by one or more component;
directing a series of samples undergoing the process in a continuous stream through the sample chamber without halting the process; and
performing a nuclear magnetic resonance measurement on the series of samples to determine at least one property of the series of samples.

18. The method as claimed in claim 17, wherein performing the nuclear magnetic resonance measurement includes performing a measurement to detect a presence of water molecules in the series of samples.

19. The method as claimed in claim 18, wherein directing the series of samples including directing a series of wood samples through the sample chamber.

20. The method as claimed in claim 17, wherein performing the nuclear magnetic resonance measurement includes determining a ratio of solid to liquid components in each sample of the series of samples.

21. A down-hole method of analyzing a fluid in an earth formation, the method comprising
providing down-hole a nuclear magnetic resonance apparatus having a sample chamber and a magnet assembly disposed about the sample chamber and constructed and arranged to provide a substantially non-uniform magnetic field having a known magnetic field gradient inside an approximate center of the sample chamber such that the substantially non-uniform magnetic field is controlled through one of a placement of at least one magnet or by one or more component;
providing a core from the earth formation, the core containing a sample of the fluid;
placing the core inside the sample chamber; and
performing down-hole a nuclear magnetic resonance measurement on the core to determine at least one property of the fluid.

22. The nuclear magnetic resonance apparatus as claimed in claim 1, wherein the one or more component is from the group consisting of at least one shield, a geometry of at least one shield, at least one material of at least one shield, at least one pole, a geometry of at least one pole, at least one material of at least one pole, a geometry of at least one magnet, at least one material of at least one magnet or any combination thereof.

23. The method as claimed in claim 17, wherein the one or more component is from the group consisting of at least one shield, a geometry of at least one shield, at least one material of at least one shield, at least one pole, a geometry of at least one pole, at least one material of at least one pole, a geometry of at least one magnet, at least one material of at least one magnet or any combination thereof.

* * * * *